United States Patent
Weems et al.

(10) Patent No.: US 11,602,426 B2
(45) Date of Patent: Mar. 14, 2023

(54) VOID OCCLUSION DEVICE

(71) Applicants: Andrew Weems, Athens, OH (US); Elizabeth Lawson, Johnson City, TN (US)

(72) Inventors: Andrew Weems, Athens, OH (US); Elizabeth Lawson, Johnson City, TN (US)

( * ) Notice: Subject to any disclaimer, the term of this patent is extended or adjusted under 35 U.S.C. 154(b) by 0 days.

(21) Appl. No.: 17/078,940

(22) Filed: Oct. 23, 2020

(65) Prior Publication Data

US 2022/0125575 A1 Apr. 28, 2022

(51) Int. Cl.
*A61F 2/12* (2006.01)

(52) U.S. Cl.
CPC ........ *A61F 2/12* (2013.01); *A61F 2210/0004* (2013.01); *A61F 2230/0091* (2013.01); *A61F 2250/0058* (2013.01)

(58) Field of Classification Search
CPC ............... A61F 2/12; A61F 2210/0004; A61F 2250/0058
USPC ........................................... 623/7–8
See application file for complete search history.

(56) References Cited

U.S. PATENT DOCUMENTS

| | | | |
|---|---|---|---|
| 5,876,446 A * | 3/1999 | Agrawal | A61F 2/40 606/76 |
| 8,480,735 B2 | 7/2013 | Rigotti et al. | |
| 9,399,122 B2 * | 7/2016 | Mosharrafa | A61M 29/02 |
| 10,524,946 B2 * | 1/2020 | Chen | A61N 1/372 |
| 10,898,313 B2 * | 1/2021 | Feinberg | B29C 41/14 |
| 2005/0015154 A1 * | 1/2005 | Lindsey | A61B 17/68 606/76 |
| 2005/0102036 A1 * | 5/2005 | Bartee | A61L 31/048 623/908 |
| 2007/0061015 A1 * | 3/2007 | Jensen | A61L 27/58 623/23.76 |
| 2008/0241212 A1 | 10/2008 | Moses et al. | |
| 2012/0239161 A1 * | 9/2012 | Datta | C08G 18/4277 623/23.72 |
| 2012/0253472 A1 * | 10/2012 | Priewe | A61L 31/04 623/23.72 |
| 2015/0057762 A1 * | 2/2015 | Harms | B29C 43/021 623/23.74 |
| 2016/0082235 A1 * | 3/2016 | Mosharrafa | A61M 29/02 606/192 |
| 2017/0095337 A1 * | 4/2017 | Pasini | A61F 2/36 |

(Continued)

FOREIGN PATENT DOCUMENTS

| | | |
|---|---|---|
| JP | 2004130118 A | 4/2004 |
| WO | WO2020/234576 A1 | 11/2020 |

OTHER PUBLICATIONS

College Station Technologies Conference, Polymers for Advanced PAT, Book of Abstracts, Aug. 8-10, 2019, 125 pages.

*Primary Examiner* — Suzette J Gherbi
(74) *Attorney, Agent, or Firm* — Standley Law Group LLP; Jeffrey S. Standley; Kenny W. Pung

(57) ABSTRACT

A void occlusion device that includes a scaffold defining a plurality of voids and a reinforcement member is described. The scaffold is configured to permit the infiltration of human tissue into the plurality of voids. The reinforcement member extends through at least a portion of the scaffold and is configured to resist compressive forces exerted on the scaffold. Also described are embodiments where the void occlusion device is biocompatible, bioresorbable, elastic, and suitable for radio imaging.

17 Claims, 15 Drawing Sheets

(56) References Cited

U.S. PATENT DOCUMENTS

| | | | |
|---|---|---|---|
| 2019/0254807 A1* | 8/2019 | Limem | A61B 90/02 |
| 2019/0343620 A1* | 11/2019 | Mlodinow | A61F 2/12 |
| 2020/0046489 A1* | 2/2020 | Feinberg | A61F 2/12 |
| 2020/0113647 A1* | 4/2020 | Hermann | A61N 5/1015 |
| 2020/0113665 A1* | 4/2020 | Priewe | A61L 27/34 |
| 2020/0115490 A1 | 4/2020 | Dove et al. | |
| 2020/0375715 A1* | 12/2020 | Egnelöv | A61F 2/0063 |
| 2020/0375726 A1* | 12/2020 | Limem | A61L 27/18 |
| 2021/0052367 A1* | 2/2021 | Yang | A61F 2/12 |
| 2021/0093444 A1* | 4/2021 | Feinberg | A61F 2/12 |
| 2021/0161645 A1* | 6/2021 | Rocco | B33Y 10/00 |
| 2021/0186678 A1* | 6/2021 | Chhaya | A61L 27/56 |
| 2021/0369912 A1* | 12/2021 | Toro Estrella | C12M 25/14 |
| 2021/0401459 A1* | 12/2021 | Gronovich | A61F 2/12 |
| 2022/0125612 A1* | 4/2022 | Chen | A61F 5/0036 |
| 2022/0133467 A1* | 5/2022 | Lazarus | A61F 2/12 623/8 |
| 2022/0133507 A1* | 5/2022 | Sanchez | A61F 2/52 623/7 |

\* cited by examiner

VOID OCCLUSION DEVICE

CROSS-REFERENCE TO RELATED APPLICATIONS

This application is a nonprovisional patent application that makes no priority claim.

FIELD

The application relates to void occlusion devices and, more particularly, to void occlusion devices that are bioresorbable and are configured to occupy the space in tissue voids.

BACKGROUND

Approximately 300,000 people in the United States, 55,000 in the United Kingdom, and 1.8 million people worldwide are diagnosed with breast cancer annually. As a result, mastectomies are commonly performed to remove the cancerous breast tissue (e.g., tumor) before it can metastasize to the rest of the body. Mastectomy procedures entail the complete removal of a human breast, which is a massively invasive surgery that causes extreme aesthetic/cosmetic changes to the patient. Further, mastectomies typically require breast reconstruction surgery following the procedure to rebuild the breast. For this reason, many patients experience not just physiological trauma, but psychological trauma as well.

As an alternative to mastectomies, lumpectomy procedures may also be performed which entails removing only the tumor instead of the whole breast. This procedure allows the surgeon to conserve much of the breast, but significantly changes the breast's shape due to the void that is created where the tumor used to be. The most frequently used method in lumpectomy treatment is to leave a surgically closed tumor-void, with the breast's shape sustained postoperatively by the fluid-filled void. However, fluid drainage may cause the void to collapse and the breast to dimple or deflate, or for the edges to heal together. This impacts the shape of the breast and often causes pain and prevents healing. An additional problem is the difficulty with precisely targeting the former tumor bed for post-operative radiotherapy, which is necessary to minimize the risk of recurrence but has the unfortunate side effect of increasing the patient's risk of secondary cancer later in life.

Nevertheless, lumpectomy procedures are generally safer, quicker, and more cost-effective than mastectomies. Despite this, more than 50% of breast cancer patients opt for mastectomies instead. One of the major reasons why patients choose mastectomies over lumpectomies is due to the failure to conserve the aesthetic shape of the breast. Clinicians also often favor mastectomy procedures because of better post-surgical radiotherapy targeting.

Accordingly those skilled in the art continue with research and development efforts in the field of lumpectomy procedures.

SUMMARY OF THE INVENTION

Disclosed are void occlusion devices that include a scaffold, a plurality of voids in the scaffold, and a reinforcement member.

In one embodiment, the void occlusion device includes a scaffold defining a plurality of voids and a reinforcement member. The scaffold is configured to permit the infiltration of human tissue into the plurality of voids. The reinforcement member extends through at least a portion of the scaffold and is configured to resist compressive forces exerted on the scaffold.

In another embodiment, the void occlusion device includes a scaffold and a reinforcement member. The scaffold includes a large disc that includes a plurality of concentric rings disposed around a center point and a plurality of radial members extending radially outwards from the center point, wherein each radial member of the large disc intersects each concentric ring of the large disc. The scaffold further includes a small disc comprising a plurality of concentric rings disposed around a center point and a plurality of radial members extending radially outwards from the center point, wherein each radial member of the small disc intersects each concentric ring of the small disc. The large disc and the small disc each define a radius, and the radius of the large disc is larger than the radius of the small disc.

In yet another embodiment, the void occlusion device includes a scaffold and a reinforcement member. The scaffold includes a latticed structure that defines a plurality of voids, wherein the scaffold is configured to permit the infiltration of human tissue into the plurality of voids. The reinforcement member extends through at least a portion of the scaffold and is configured to resist compressive forces exerted on the scaffold.

Other examples of the disclosed void occlusion device, and method of making the same, will become apparent from the following detailed description, the accompanying drawings and the appended claims.

DETAILED DESCRIPTION

Figure 1:
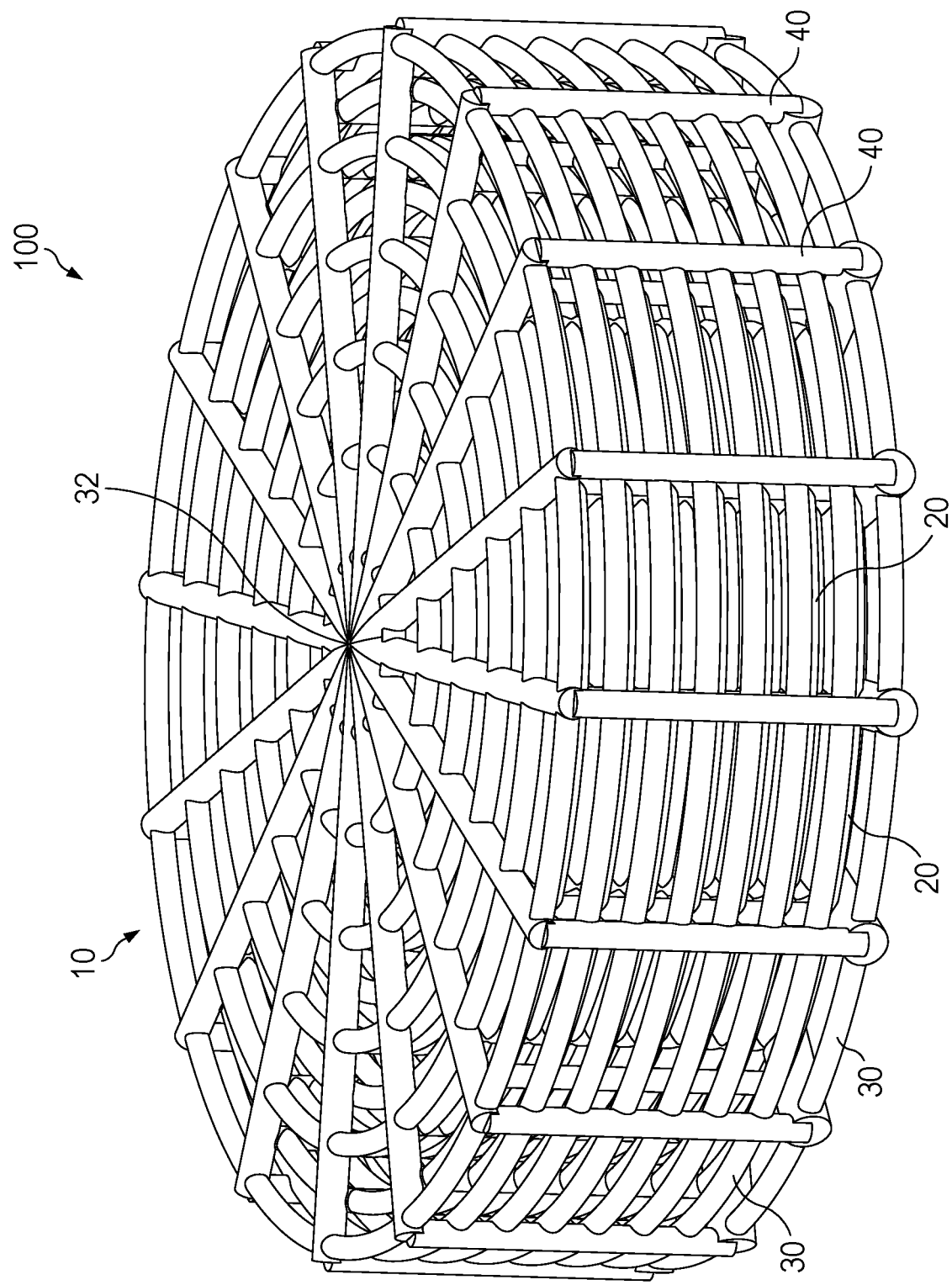
FIG. 1 is a top perspective view of a first embodiment of the void occlusion device.

The following detailed description refers to the accompanying drawings, which illustrate specific examples described by the disclosure. Other examples having different structures and operations do not depart from the scope of the present disclosure. Like reference numerals may refer to the same feature, element, or component in the different drawings.

Illustrative, non-exhaustive examples, which may be, but are not necessarily, claimed, of the subject matter according the present disclosure are provided below. Reference herein to "example" means that one or more feature, structure, element, component, characteristic and/or operational step described in connection with the example is included in at least one embodiment and/or implementation of the subject matter according to the present disclosure. Thus, the phrase "an example" and similar language throughout the present disclosure may, but do not necessarily, refer to the same example. Further, the subject matter characterizing any one example may, but does not necessarily, include the subject matter characterizing any other example.

Referring to FIG. 1, the present disclosure provides an embodiment of a void occlusion device 100 (herein, "the device") that may be utilized to aid in the cosmetic restoration of a human breast. When a void is created in a human breast, the device 100 may be implanted into that void to provide mechanical support to the overlaying breast tissue (e.g., fat cells, blood vessels, and other native cells), thereby maintaining the natural contouring of the breast (e.g., size and shape). The device 100 includes a scaffold 10, comprising a porous structure, that permits infiltration of natural breast tissue therein (i.e., ingrowth). After a period of time, the device 100 may be eroded by the body (i.e., bioresorbable) leaving only natural breast tissue in the space where the void used to be.

Figure 4:
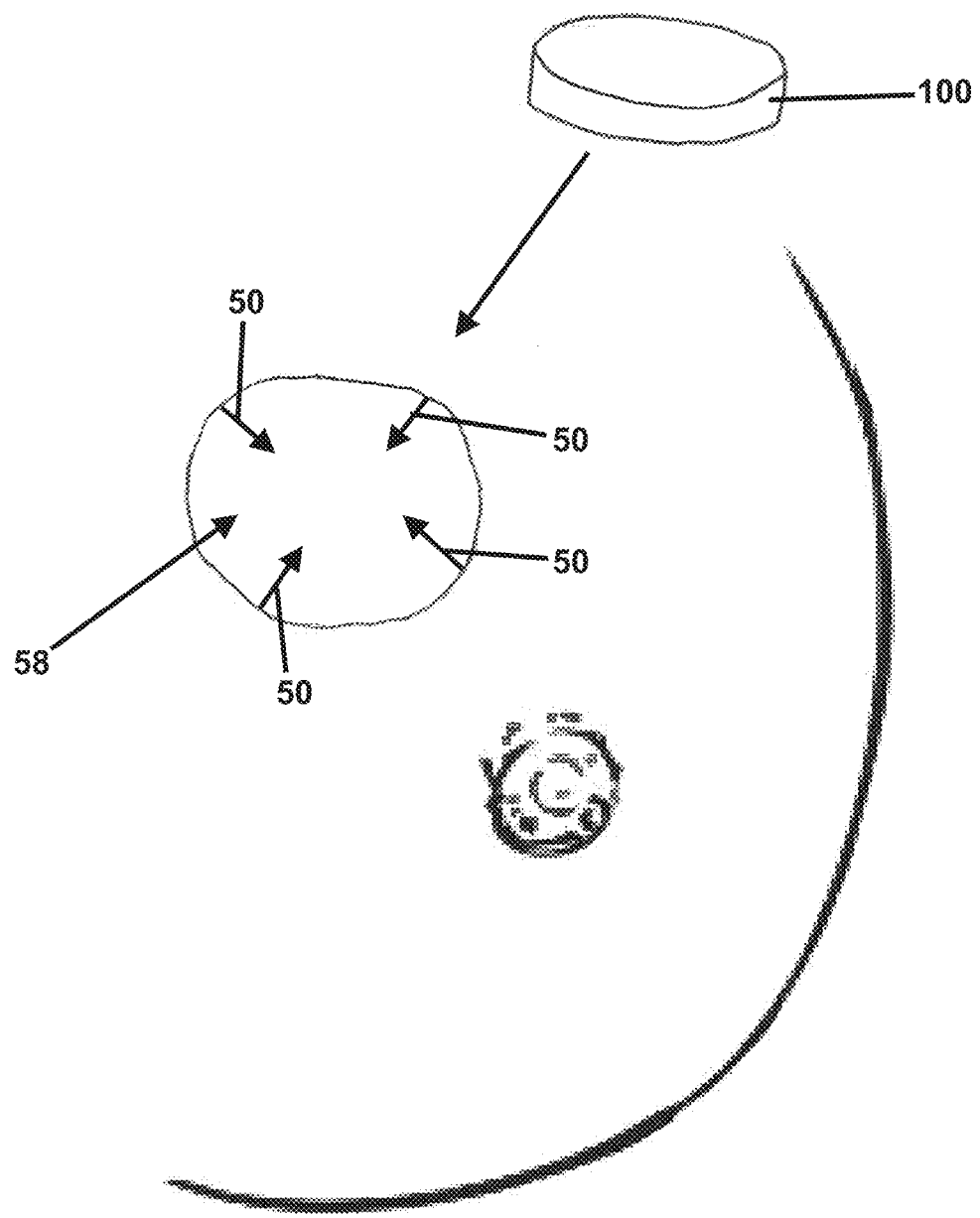
FIG. 4 is a schematic illustration of the void occlusion device of FIG. 1 being inserted into a void in a human breast.
Figure 5:
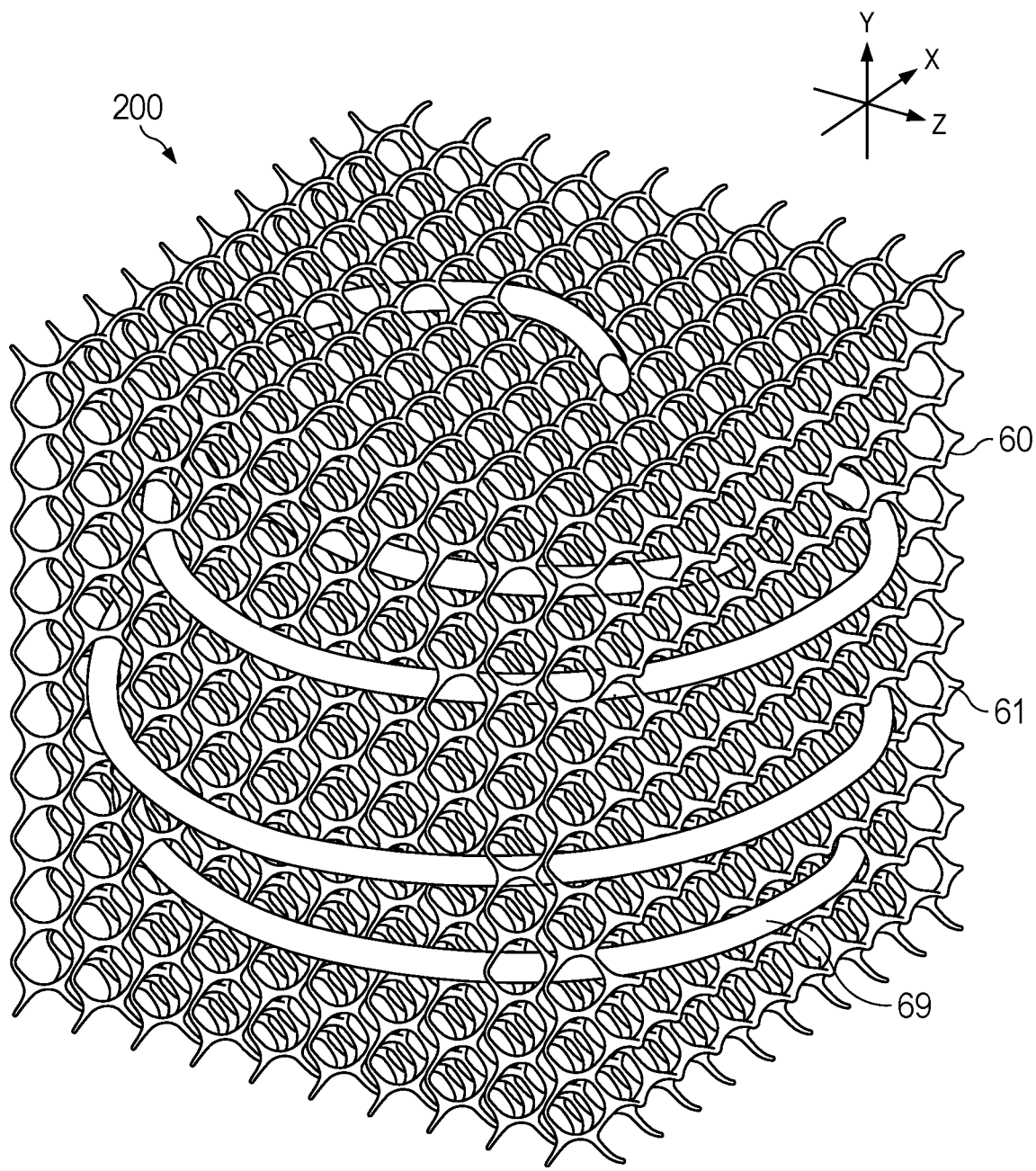
FIG. 5 is a top perspective view of a second embodiment of the void occlusion device.
Figure 6:
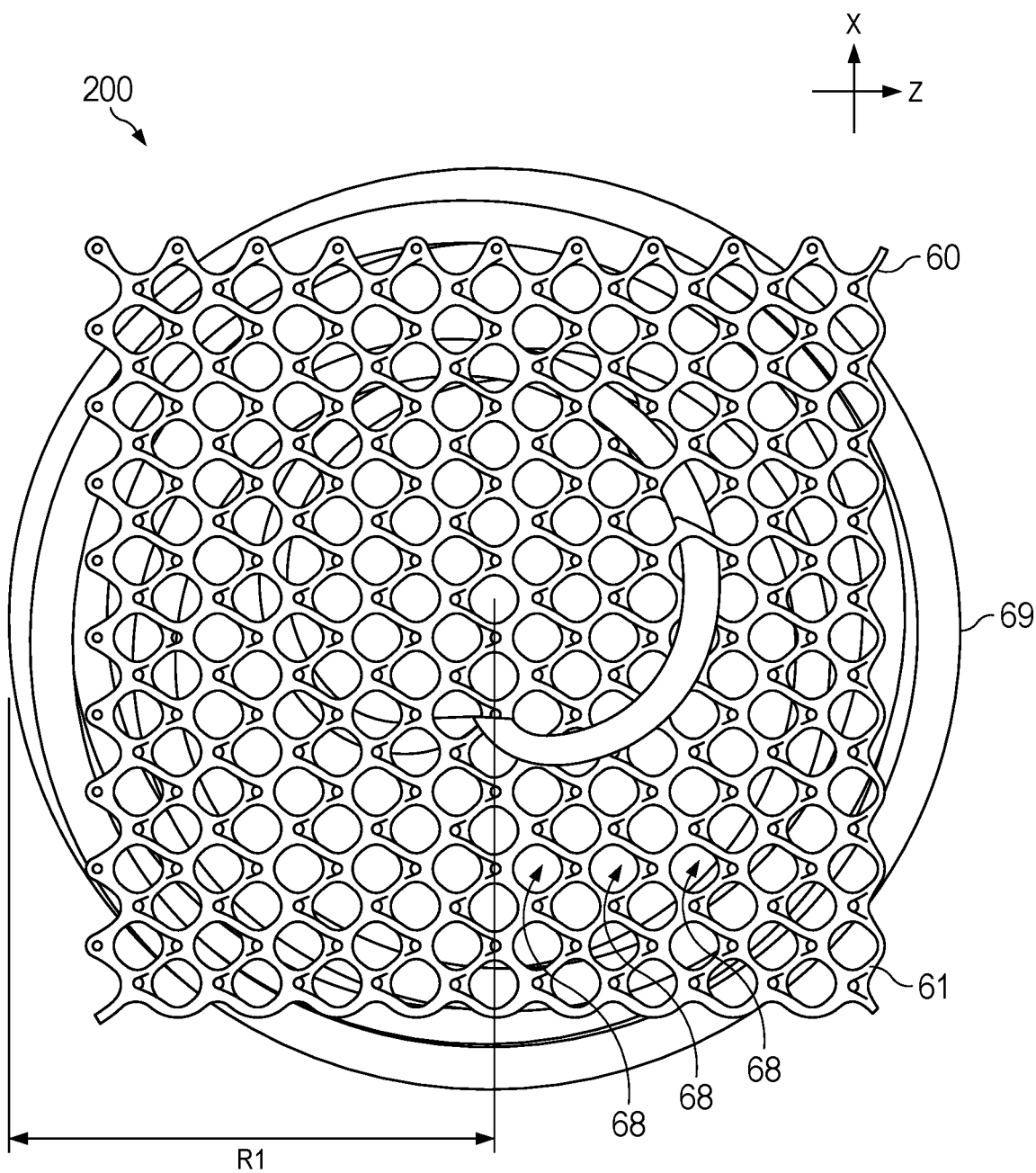
FIG. 6 is a top plan view of the void occlusion device of FIG. 6.

Particularly in the context of lumpectomy procedures, the device 100 may be useful for filling voids 58 created by the removal of a tumor (FIG. 4). The device may be inserted during the same procedure following tumor removal. Doing so may facilitate the healing of the breast without the risk of collapse or dimpling, thereby improving the patient's quality of life. Further, given the bioresorbability of the device 100, it is contemplated that little to no subsequent reconstruction of the breast would be required. Additionally, as described below, the device 100 may also aid in the radio imaging of the tumor site following the lumpectomy.

The device 100 may similarly be used for breast augmentation and enhancement. Breast enhancement is typically performed by separating breast tissue from the underlying musculature and connective tissue to create a pocket either in front of or behind the pectoral muscle. A conventional breast implant (e.g., saline or silicone filled) is then inserted into the pocket and the site is closed. Here, the device 100 may be inserted into the pocket like a conventional breast implant to achieve the patient's desired size and shape. Moreover, it is generally contemplated that the device 100 may present several improvements over conventional breast implants. For example, since the device 100 is mostly comprised of a porous structure, and does not contain a quantity of saline or silicone gel, the device 100 may be less dense and more lightweight than conventional breast implants. Thus, the risk of leakage is eliminated and the likelihood of sagging is minimized. Further, since the device 100 is designed to be eroded by the body, leaving behind only natural breast tissue, the end result will be a breast that looks and feels more natural, if not completely natural. In contrast, conventional breast implants are typically distinctive in feel, which may cause issues with palpitation and even imagining during breast cancer screenings.

Referring to FIGS. 1-3, 5-9, and 10-14, the present disclosure provides three non-limiting embodiments of the device. Each of these embodiments are discussed in turn below.

Figure 2:
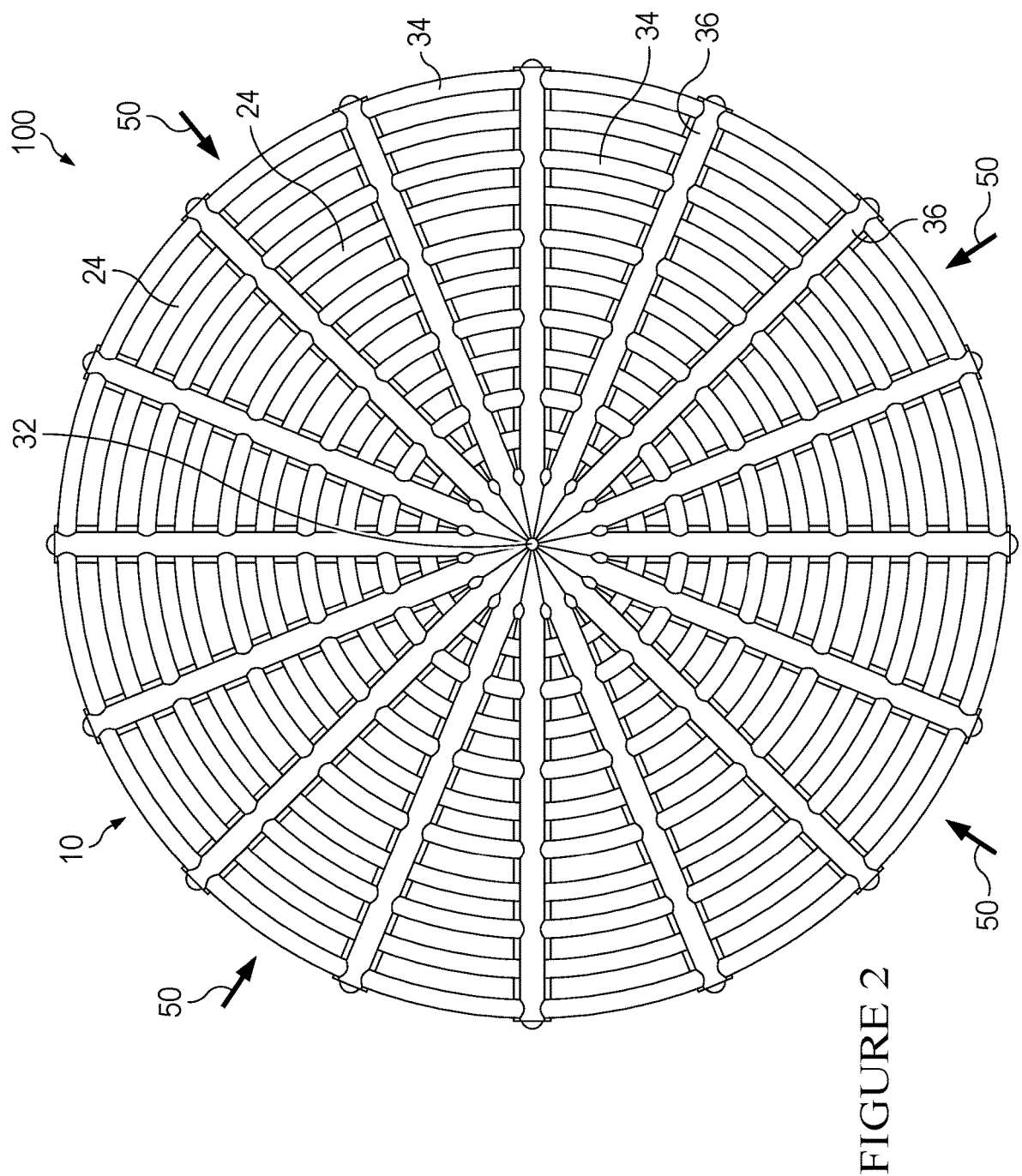
FIG. 2 is a top plan view of the void occlusion device of FIG. 1.
Figure 3:
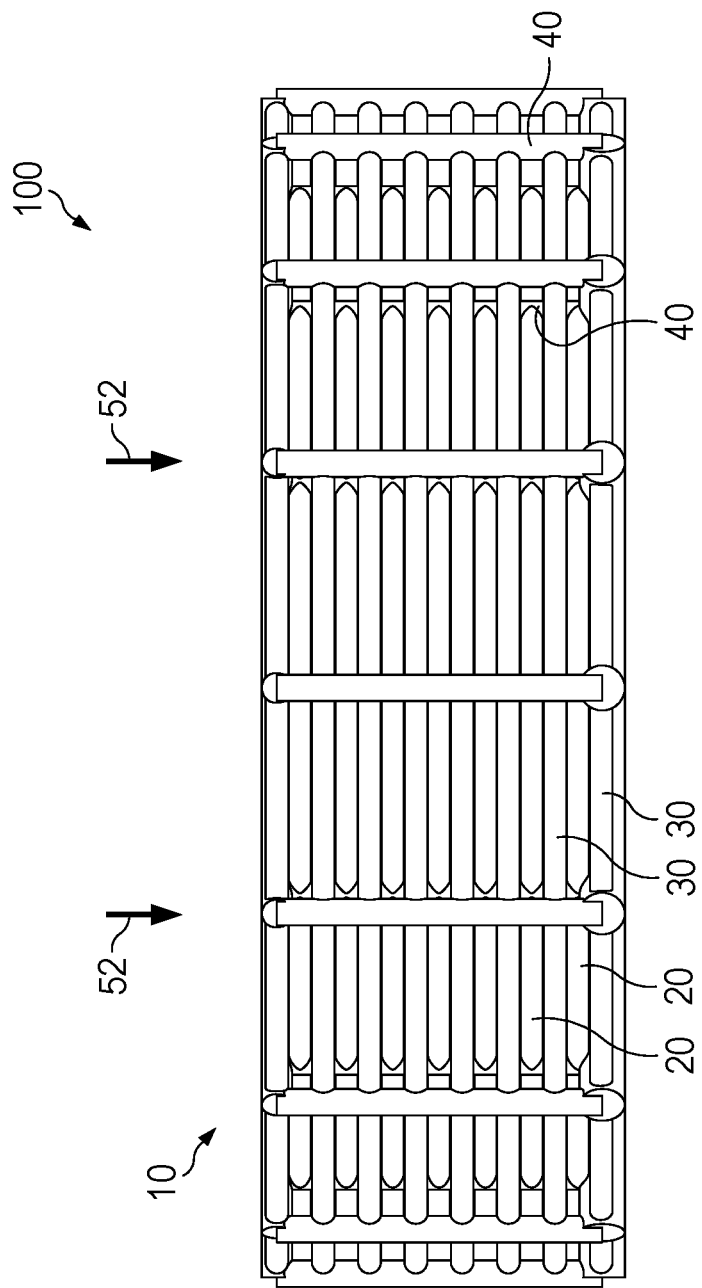
FIG. 3 is a side elevational view of the void occlusion device of FIG. 1.

Referring to FIGS. 1-3, a first embodiment is shown. Here, the device 100 includes a scaffold 10 that defines an overall cylindrical shape, comprised of alternating units of small 20 and large discs 30 (FIG. 3). These discs 20, 30 are arranged in a stacked configuration and aligned along their center points 22, 32.

The large discs 30 may each include a plurality of concentric rings 34 (six being shown) connected by a plurality of radial members 36 (sixteen being shown). The radial members 36 may extend from the center point 32 to the outermost concentric ring 34. Further, each concentric ring 34 may be incrementally larger than the concentric ring 34 immediately before it (i.e., closer to the center point).

The small discs 20 have a smaller radius than the large discs 30, but may otherwise be similar in configuration. That is to say, the small discs 20 may also include a plurality of concentric rings 24 (five being shown) connected by a plurality of radial members 26 (sixteen being shown) extending radially outwards from a center point 22. As arranged, the radial members 26 may align with the radial members 36 of the large discs 30. Further, the concentric rings 24 of the small discs 20 may be disposed in an offset arrangement relative to the concentric rings 34 of the large discs 30. As shown in FIG. 2, when viewed from above, the concentric rings 24 of the small discs 20 may occupy the horizontal space between the concentric rings 34 of the large discs 30.

Further, the device may include a plurality of reinforcement members 40 extending perpendicular from the plane of each disc 20, 30. These reinforcement members 40 may extend from where the concentric rings 24, 34 intersect with the radial members 26, 36. In the embodiment shown, reinforcement members 40 are provided at each concentric ring-radial member intersection, and are generally equal in size and shape.

As those skilled in the art will appreciate, the radial members 26, 36 of the discs 20, 30 may resist longitudinal compression 50 of the device 100 (FIG. 3), whereas the reinforcement members 40 resist lateral compression 52 (FIG. 2). In this way, the device 100 may prevent a breast void 58 from collapsing in on itself while also providing the necessary support to maintain its shape (FIG. 4).

Figure 9:
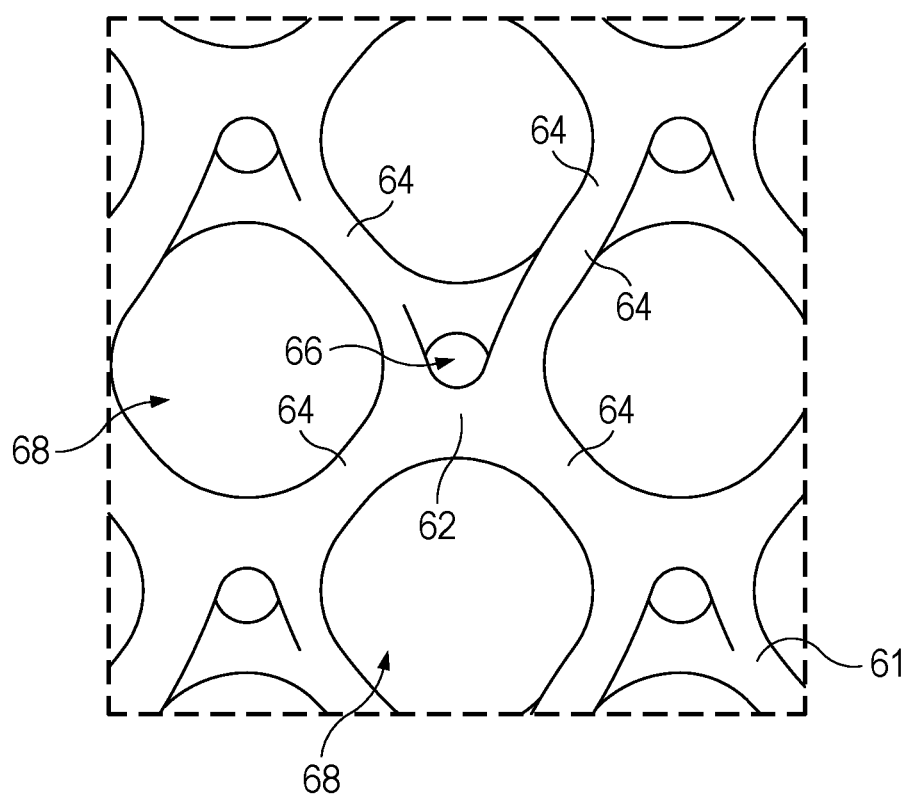
FIG. 9 is a side elevational view of a portion of the void occlusion device of FIG. 6.
Figure 10:
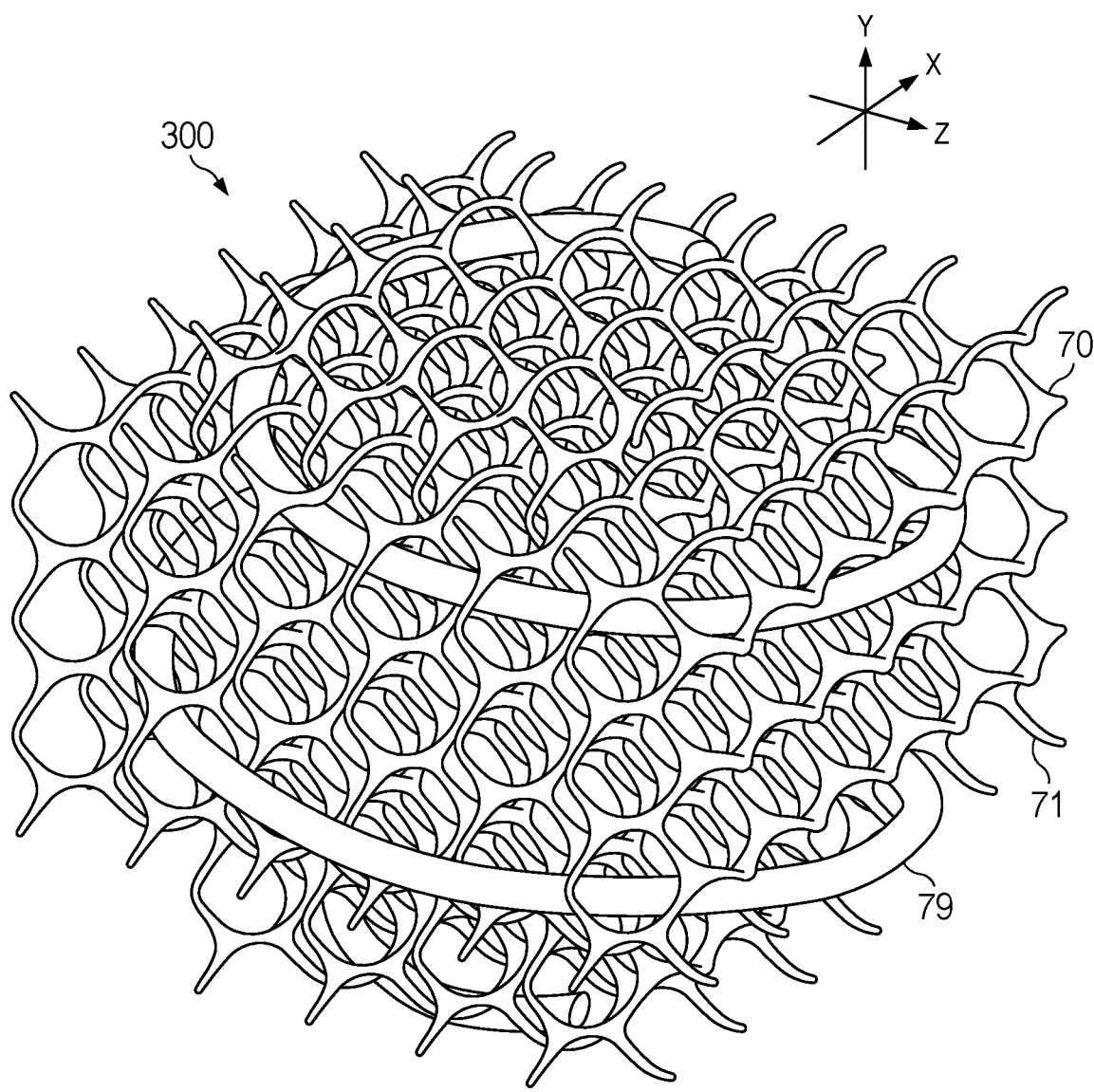
FIG. 10 is a top perspective view of a third embodiment of the void occlusion device.
Figure 11:
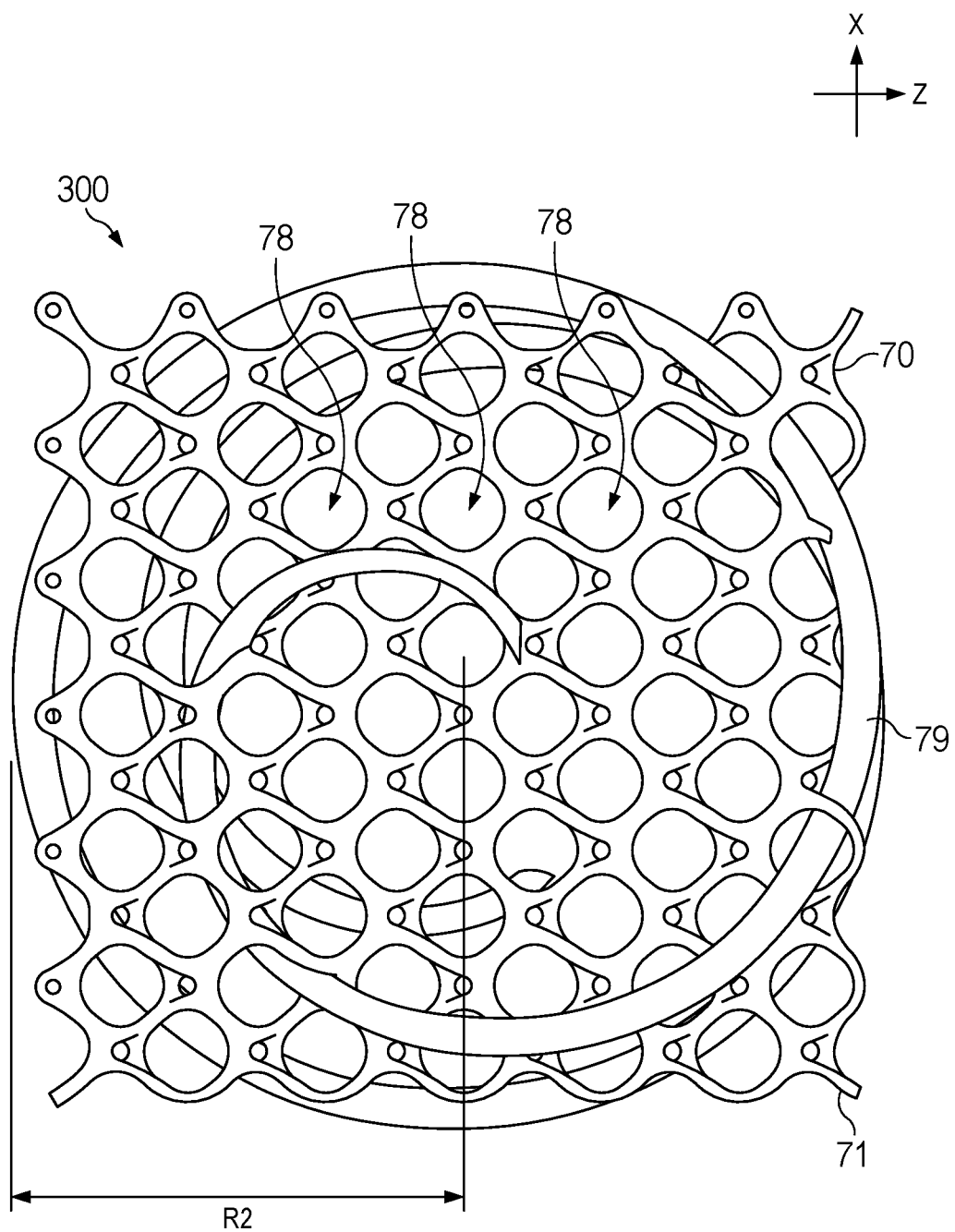
FIG. 11 is a top plan view of the void occlusion device of FIG. 11.
Figure 12:
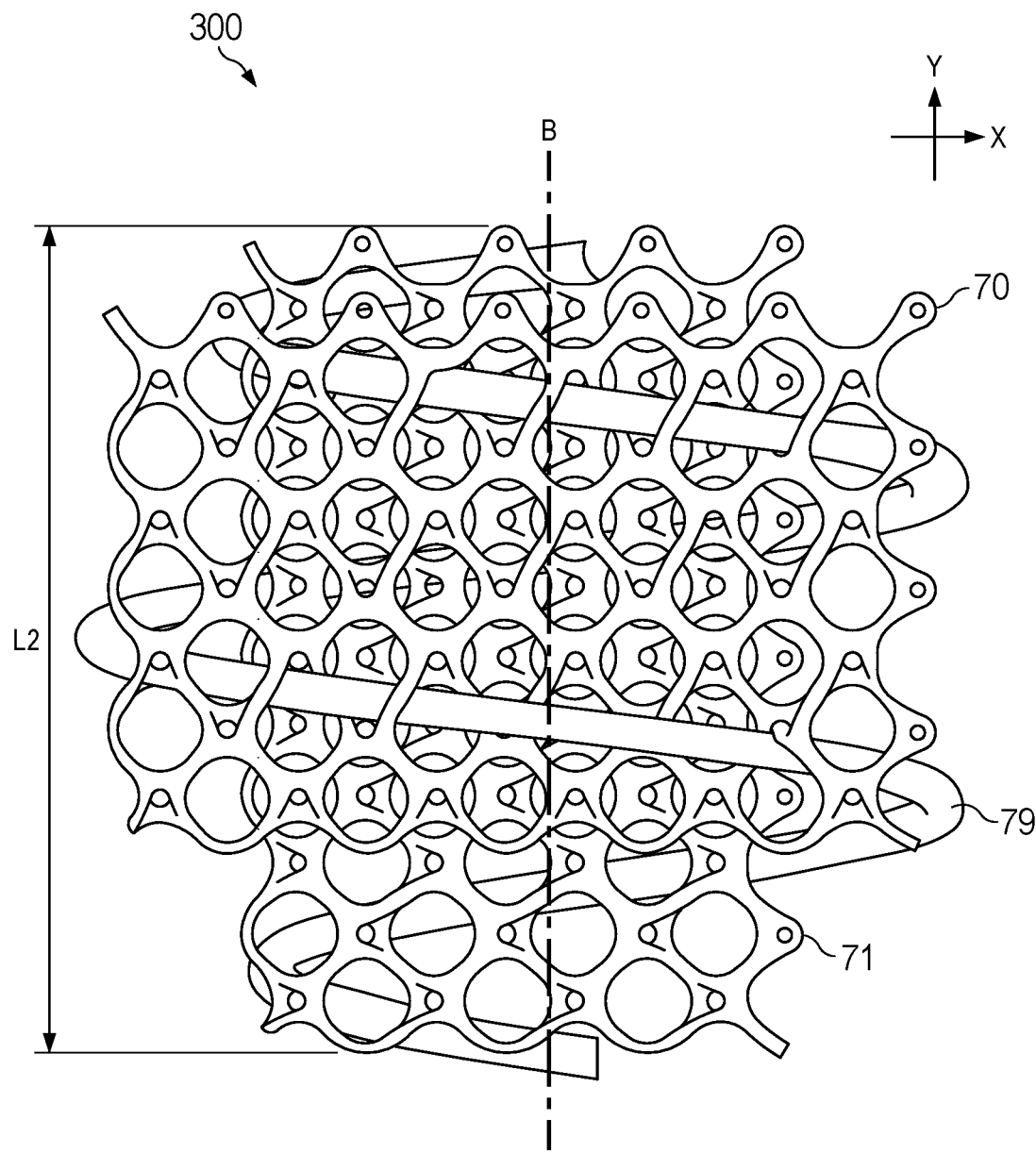
FIG. 12 is a side elevational view of the void occlusion device of FIG. 11.
Figure 13:
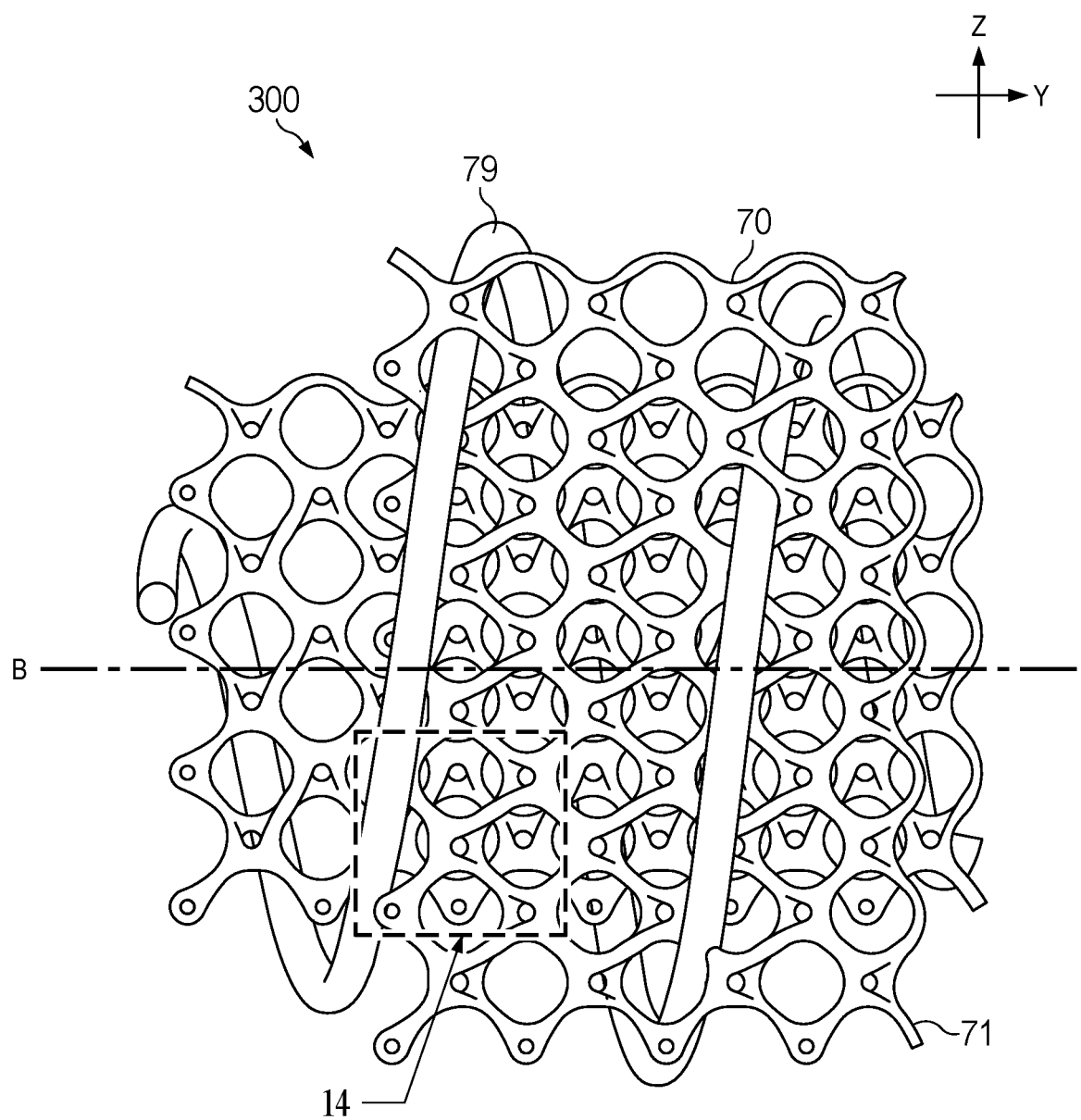
FIG. 13 is an alternate side view of the void occlusion device of FIG. 11.

Referring to FIGS. 5-9, a second embodiment of the device 200 is shown. Here, the device 200 includes a scaffold 60 that comprises a uniform latticed structure 61. Each unit cell of the latticed structure 61 comprises a center portion 62 with six branching arms 64 and a pore 66 extending through the center portion 62 (FIG. 9). The center portion 62 and the branching arms 64 may be curved such that circular channels 68 are defined throughout the device 200. In the embodiment shown, circular channels 68 are defined from each cartesian direction (X in FIG. 7, Y in FIG. 6, and Z in FIG. 8). These channels 68 provide a clear path for the growth of new breast tissue into the device, thereby facilitating infiltration. In one exemplary embodiment, each unit cell may occupy a space that is about 0.5 cubic millimeters to about 2.0 cubic millimeters.

Figure 7:
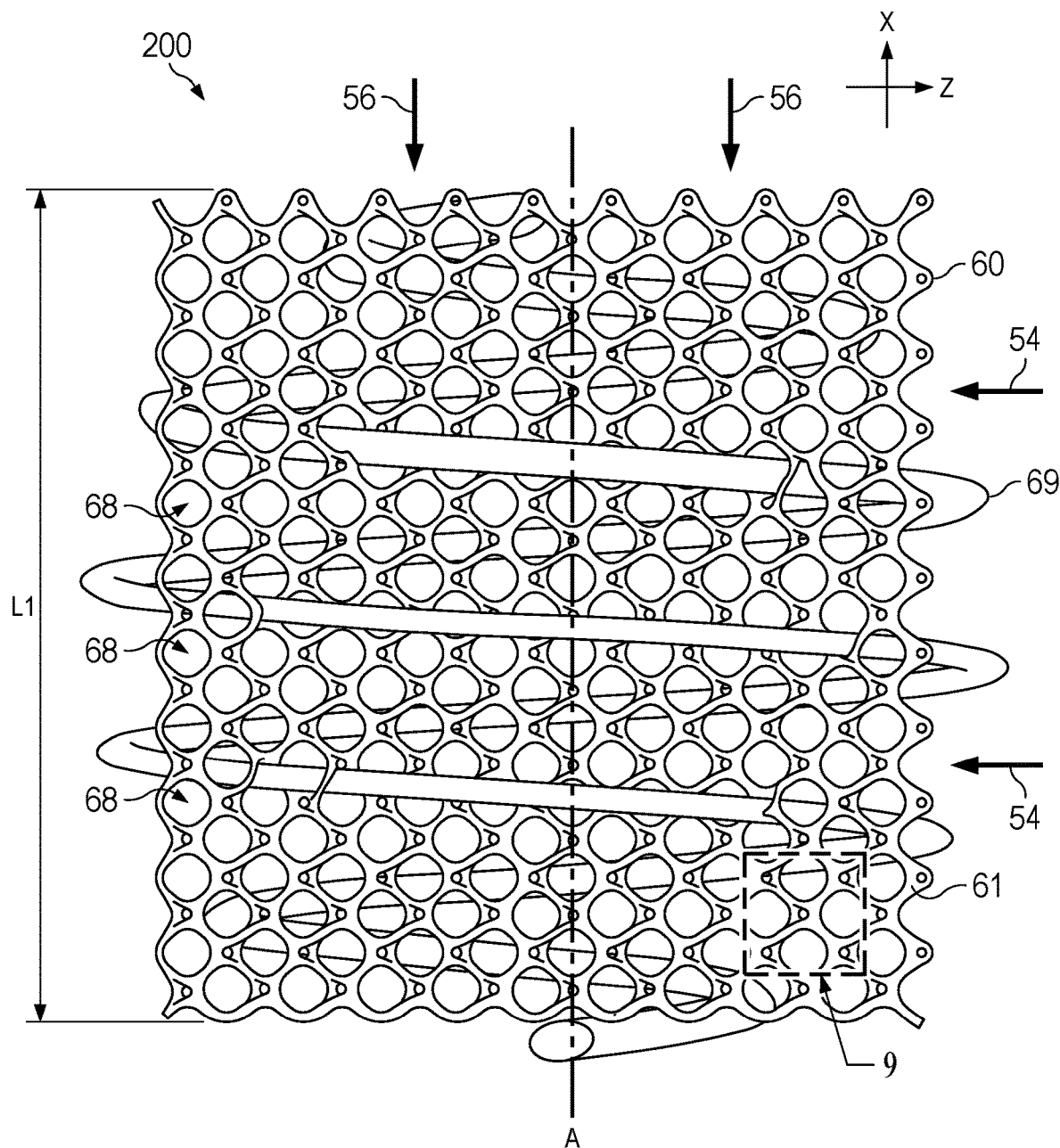
FIG. 7 is a side elevational view of the void occlusion device of FIG. 6.
Figure 8:
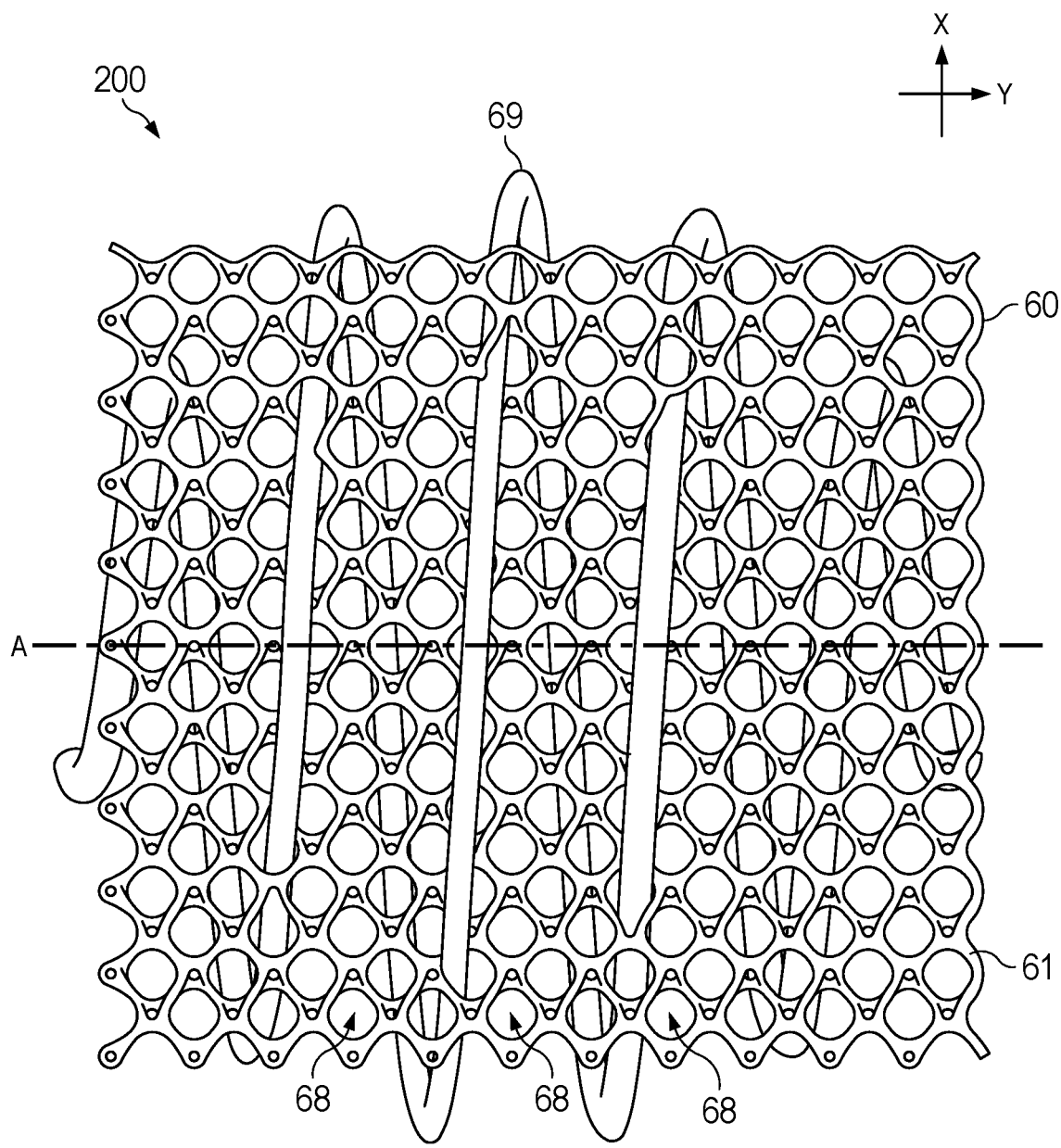
FIG. 8 is an alternate side elevational view of the void occlusion device of FIG. 6.

Further, a reinforcement member 69 may also be provided to resist compression. Here, the reinforcement member 69 comprises a spiral extending through, and is integral with, the scaffold 60. As those skilled in the art will appreciate, this spiral may resist compressive forces lateral 54 to the axis A of the spiral (FIG. 7). Parallel forces 56 may face less resistance, thereby contributing to a softer feel. In one example, the reinforcement member 69 may have a spiral radius $R_1$ of about 4 millimeters to about 40 millimeters. In another example, the reinforcement member 69 may have a spiral length $L_1$ of about 4 millimeters to about 40 millimeters.

Figure 14:
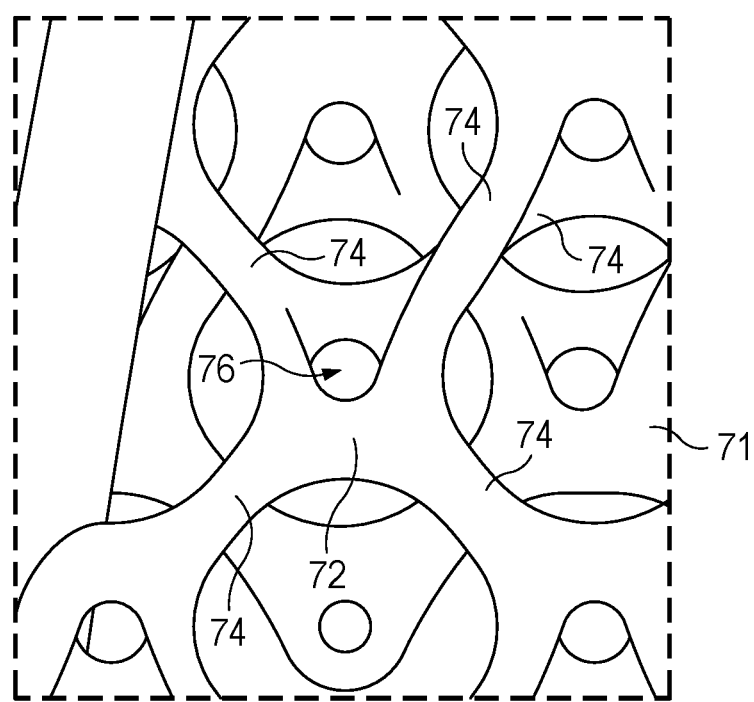
FIG. 14 is a side elevational view of a portion of the void occlusion device of FIG. 11.

Referring to FIGS. 10-14, a third embodiment of the device 300 is shown. This device 300 is similar to the device 200 of the second embodiment in that also includes a scaffold 70 that comprises a uniform latticed structure 71 and a spiral reinforcement member 79 extending through it. In one example, the reinforcement member 79 may have a spiral radius $R_2$ of about 4 millimeters to about 40 millimeters. In another example, the reinforcement member 79 may have a spiral length $L_3$ of about 4 millimeters to about 40 millimeters. Further, each unit cell of the third embodiment also includes a center portion 72 with six branching arms 74 and a pore 76 extending through the center portion 72 (FIG. 14). However, the lattice structure 71 of the third embodiment 300 differs from the lattice structure of the second embodiment 200 in that the branching arms 74 and the center portions 72 are curved such that channels 78 are only provided from one cartesian direction (Y in FIG. 11). As those skilled in the art will appreciate, orienting the center portions 72 in this way may enable the device to resist compressive forces parallel 56 to the axis of the reinforcement member spiral.

The device 100, 200, 300 may scaled, shaped, and/or combined as needed to accommodate voids of any size and shape. For example, the device of the first embodiment 100 may be scaled up in size to accommodate particularly large voids. In another example, the device of the second embodiment 200 may be comprise a repeat unit in a larger void occlusion device. In yet another embodiment, the device of the third embodiment 300 may be cut (i.e., shaped) or otherwise manipulated by a clinician to match the shape of a void. Any of the principles illustrated in the above three examples may be applied to any of the three embodiments of the device 100, 200, 300.

While the above three embodiments of the device 100, 200, 300 are exemplary, it is contemplated various other designs and configurations for the scaffold and the reinforcement member may be utilized without departing from the scope of the present disclosure, so long as the overall device 100 is porous enough for natural breast tissue to infiltrate. For example, porous, irregular designs that do not include a defined latticed structure comprised of repeating unit cells may also be employed. These designs may be preferable for embodiments where the device 100 is fabricated from foam-based materials.

By necessity, the device 100 must be fabricated from biocompatible (e.g., cytocompatible) materials. Failure to do so may result in pain, discomfort, or worse to the patient, especially considering as how the device 100 is intended to remain inside the patient long term. Further, the material selected should also exhibit bioresorbable properties (i.e., the material will be taken up by the body when implanted rather than remaining inert at the implant site) so as to enable the device 100 to be degraded by the patient over time. Preferably, the device 100 may slowly degrade within the body over a period of time ranging from 12 months to 48 months, but ideally between 18 months and 24 months. Further, the material may also be 3D printable to facilitate the fabrication of the complex latticed structures shown in FIGS. 1-14. Additionally, the material may also be elastic, exhibiting a low force of expansion and preferably a strain to failure measure ranging from 20% to nearly 300%, such that the device may be compressed prior to being implanted, and then may gently expand to fill the void and take on the void shape without expanding or tearing the soft surrounding tissue (e.g., shape memory).

The ideal material for the lumpectomy and breast enhancement applications will be a soft, flexible polymer which can be processed using additive manufacturing (preferably compatible with the PCResink platform) or traditional manufacturing techniques, is capable of withstanding deformations resulting from tissue distortion both during the surgery and during everyday life, and which acts as a tissue scaffold (chemical guiding or inert) to allow for healing to take place across the void site after which the device will degrade away (hydrolytic, enzymatic or oxidative degradation behavior). Additional ideal characteristics include radio-visibility under clinical x-ray imaging, ability to withstand sterilization, and the ability to process as a composite as well as the original material formulation.

One such example of a suitable material is an aliphatic polycarbonate, which displays a low elastic modulus and elastomeric behavior, may be processed using digital light processing or stereolithography, and is suitable for tissue infiltration prior to a slow surface erosion degradation over the course of 18-24 months. A second suitable material would be aliphatic polyester, where sufficient crystalline content could be used to produce a flexible, tough material capable of being processed using 3D printing into a porous tissue scaffolding device which would slowly degrade as healing takes place.

While the exact composition of such an aliphatic polycarbonate and/or aliphatic polyester may vary without departing from the scope of the present disclosure, it is contemplated that a suitable material may generally include, for example, polycarbonate linkages, diluents (e.g., reactive and/or nonreactive), and crosslinkers. Examples of suitable polycarbonate linkages may include, without limitation, phosphor-ester linkages, polyester linkages, polyurethane linkages, amide linkages, urea linkages, sulphide linkages, disulphide linkages, thioester linkages, dithioester linkages, thioester linkages, and/or a hydrocarbon backbone. Examples of suitable diluents may include functional groups such as, but not limited to, thiols, alkynes, azides, cyclic carbonates, propylene carbonate, small molecule epoxides, alkenes, thiols, and/or hybrid molecules containing any combination of the aforementioned functional groups. Examples of a suitable crosslinker may include, without limitation, a thiol crosslinker, multi-armed thiol crosslinkers and, more preferably, pentaerythritol tetrakis(3-mercaptopropionate).

In another embodiment, a suitable material may include drug-derived monomers such as a monomer derived from one or more of the following non-steroidal anti-inflammatory drug (NSAID) classes: salicylates, propionic acid derivatives, acetic acid derivatives, enolic acid (oxicam) derivatives, anthranilic acid derivatives (fenamates), selective COX-2 inhibitors, sulfonanilides, and others. Specific examples of NSAIDs that fall within these classes, which may be suitable here, may include: Aspirin (acetylsalicylic acid), Diflunisal (Dolobid), Salicylic acid and its salts, Salsalate (Disalcid), Ibuprofen, Dexibuprofen, Naproxen, Fenoprofen, Ketoprofen, Dexketoprofen, Flurbiprofen, 15 Oxaprozin, Loxoprofen, Indomethacin, Tolmetin, Sulindac, Etodolac, Ketorolac, Diclofenac, Aceclofenac, Nabumetone, Piroxicam, Meloxicam, Tenoxicam, Droxicam, Lornoxicam, Isoxicam, Phenylbutazone (Bute), Mefenamic acid, Meclofenamic acid, Flufenamic acid, Tolfenamic acid, Celecoxib, Rofecoxib, Valdecoxib, Parecoxib, Lumiracoxib; Etoricoxib, Firocoxib, Nimesulide, Clonixin, Licofelone, and/or 35 H-harpagide.

Moreover, the material may also include one or more photoinitiators such the resulting composition is photocurable. An example of a suitable photoinitiator may include, without limitation, Irgacure® 784 (IUPAC name: Bis(.eta.5-2,4-cylcopentadien-1-yl)-bis(2,6-difluoro-3-(1H-pyrrol-1-yl)-phenyl) titanium), an iodonium salt, a silyl or germane initiator (e.g. tris(trimethylsilyl)germane), tris(trimethylsilyl)silane (TTMS), Omnirad® 369 (IUPAC name: 2-Benzyl-2-dimethylamino-1-(4-morpholinophenyl)-butanone-1), Irgacure® 819 (IUPAC name: bis(2,4,6-trimethylbenzoyl)-phenylphosphineoxide), H—Nu 640® (a cyanine borate photoinitiator available from Spectra Group Limited, Inc. 27800 Lemoyne Rd., Suite J Millbury, Ohio 43447) and/or Sylanto 7MP (a proprietary diaryliodonium salt with a hexafluorphosphate anion available from Synthos Specialities, Synthos Spólka Akcyjna, Chemików 1, 32-600 Oświęcim, Poland).

Figure 15:
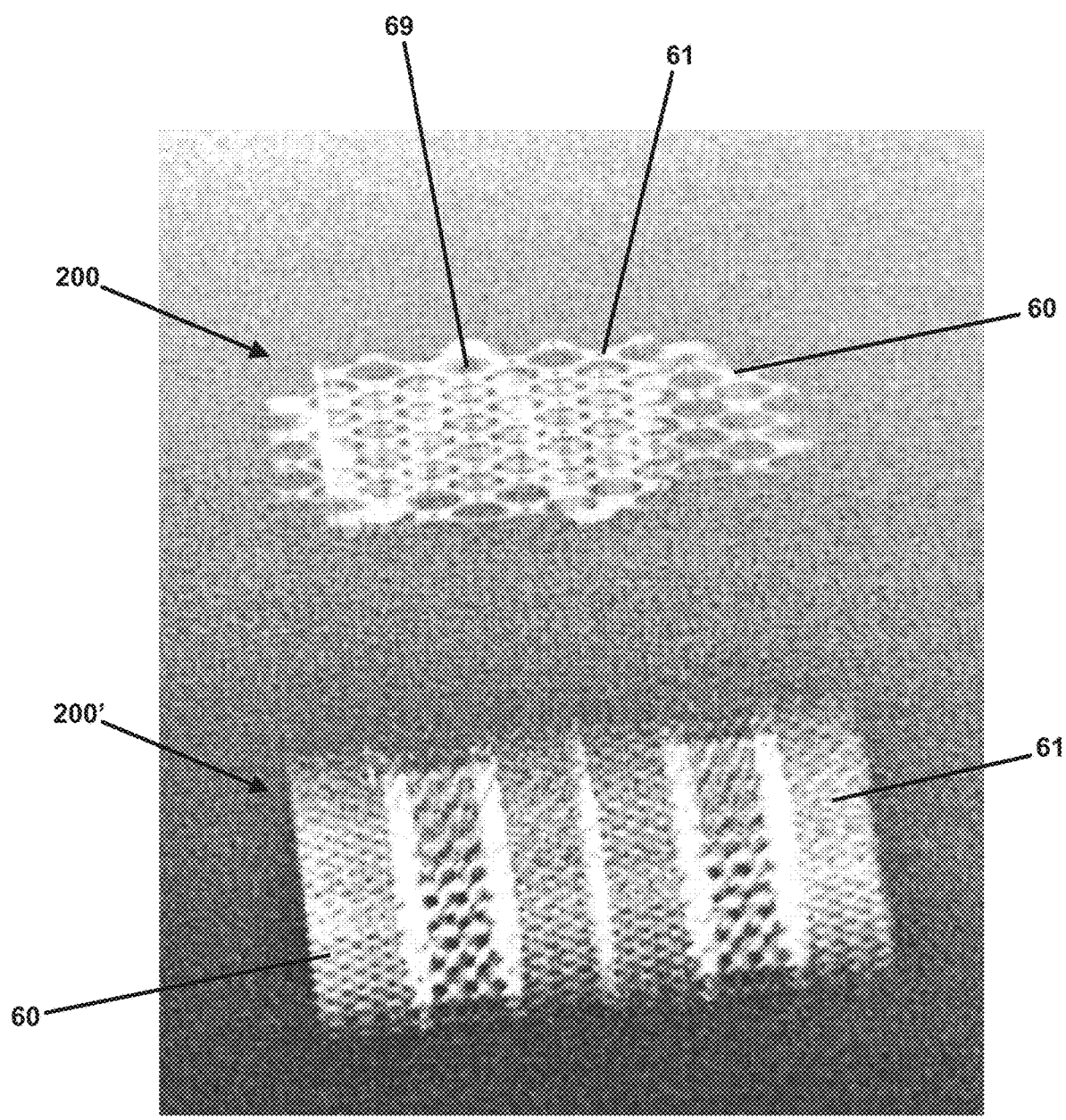
FIG. 15 is an X-ray image showing two embodiments of the void occlusion device that were taken under conventional clinical imaging.

Referring to FIG. 15, which depicts two devices of the second embodiment (one device 200 with a spiral reinforcement member 69 and the other device 200' without), it is shown that the design of the device provides for excellent radio-visibility when viewed under x-ray. In effect, the device 100 may be used as an in-body target to increase the accuracy of post-operative radiotherapy, thereby reducing the risk of secondary cancer formation caused by extended or untargeted radiation exposure. By using the present invention as a visual target for medical treatment radiation therapy, the precise zone in which the lumpectomy procedure removed cancerous tissue can be treated, while limiting radiation exposure outside that precise treatment zone, thereby making radiation therapy more effective by targeting the precise zone where the cancer had been, and more safe for the patient by not exposing the patient to radiation outside the precise zone, or at a minimum limiting the radiation exposure beyond the invention location zone in the patient's body. Further, it is additionally contemplated that the scaffold and/or the reinforcement member may be modified with materials such as metallic micro/nano particles or with heavy atoms (e.g., iodine) to further improve the radio-visibility of the device.

The device, including the embodiments of the device 100, 200, 300 described above, may be fabricated by way of any suitable method such as, but not limited to, additive manufacturing. In a preferred embodiment, the device may be fabricated by formulating a polycarbonate resin, tunable by adjusting various compositions of oligomers, crosslinkers, reactive diluents, and chain extenders, and feeding the resin through a 3D printing machine to additively manufacture the device. Even more preferably, the resin may be a 4D polycarbonate resin ink (PCResink), ideally reproducible at a 1 liter scale, that is compatible with the PCResink platform. As those skilled in the art will appreciate, such a material is capable of being 3D printed and while also possessing the ability to change its shape in response to external stimulus. The PCResink platform may be capable of large void filling behaviors without exerting substantial expansion forces which would distort soft tissues.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A void occlusion device comprising:
   a breast implantable scaffold comprising a latticed structure defining a plurality of voids, wherein the scaffold is configured to permit the infiltration of human tissue into the plurality of voids; and
   a radial shaped reinforcement member extending through at least a portion of the scaffold, wherein the reinforcement member is configured to resist compressive forces exerted on the scaffold.

2. The void occlusion device of claim 1 wherein the scaffold comprises a material composition that is biocompatible.

3. The void occlusion device of claim 1 wherein the scaffold is bioresorbable over a period of time ranging from 12 months to 48 months.

4. The void occlusion device of claim 1 wherein the scaffold comprises a strain to failure ranging from 20% to 300%.

5. The void occlusion device of claim 1 wherein said device is visible under x-ray.

6. The void occlusion device of claim 1 wherein the scaffold comprises a material composition comprising aliphatic polycarbonate oligomers.

7. The void occlusion device of claim 1 wherein the scaffold is fabricated from a 3D printable polycarbonate.

8. A void occlusion device comprising:
   a scaffold defining a plurality of voids, wherein the scaffold is configured to permit the infiltration of human tissue into the plurality of voids, the scaffold comprising:
      a large disc comprising a plurality of concentric rings disposed around a center point and a plurality of radial members extending radially outwards from the center point, wherein each radial member of the large disc intersects each concentric ring of the large disc;
      a small disc comprising a plurality of concentric rings disposed around a center point and a plurality of radial members extending radially outwards from the center point, wherein each radial member of the small disc intersects each concentric ring of the small disc; and
      wherein the large disc and the small disc each define a radius, and the radius of the large disc is larger than the radius of the small disc; and
   a reinforcement member extending through at least a portion of the scaffold, wherein the reinforcement member is configured to resist compressive forces exerted on the scaffold.

9. The void occlusion device of claim 8 wherein:
   the large disc and the small disc are arranged in a stacked configuration; and
   the center point of the large disc is aligned with the center point of the small disc.

10. The void occlusion device of claim 8 wherein the reinforcement member extends perpendicular from at least one of the large disc and the small disc.

11. The void occlusion device of claim 8 wherein the concentric rings of the large disc are offset relative to the concentric rings of the small disc.

12. A void occlusion device comprising:
- a scaffold comprising a latticed structure that defines a plurality of voids, wherein the scaffold is configured to permit the infiltration of human tissue into the plurality of voids, and wherein the scaffold comprises a bioresorbable aliphatic polyester material composition; and
- a reinforcement member extending through at least a portion of the scaffold, wherein the reinforcement member is configured to resist compressive forces exerted on the scaffold wherein the reinforcement member comprises a spiral.

13. The void occlusion device of claim 12, wherein the latticed structure comprises a unit cell comprising a center portion and a plurality of branching arms extending from the center portion.

14. The void occlusion device of claim 13 wherein the center portion and the branching arms are curved such that channels are defined through the latticed structure from each cartesian direction.

15. The void occlusion device of claim 13 wherein the center portion and the branching arms are curved such that channels are device through the latticed structure from one direction.

16. The void occlusion device of claim 13 wherein the unit cell further comprises a pore extending through the center portion.

17. The void occlusion device of claim 1, wherein the device is comprised of a shape memory material.

\* \* \* \* \*